United States Patent
Gill et al.

(10) Patent No.: US 6,840,251 B2
(45) Date of Patent: Jan. 11, 2005

(54) METHODS OF SIMULTANEOUSLY CLEANING AND DISINFECTING INDUSTRIAL WATER SYSTEMS

(75) Inventors: Jasbir S. Gill, Naperville, IL (US); Amit Gupta, Aurora, IL (US)

(73) Assignee: Nalco Company, Naperville, IL (US)

(*) Notice: Subject to any disclaimer, the term of this patent is extended or adjusted under 35 U.S.C. 154(b) by 83 days.

(21) Appl. No.: 10/409,220

(22) Filed: Apr. 8, 2003

(65) Prior Publication Data

US 2003/0200997 A1 Oct. 30, 2003

Related U.S. Application Data

(63) Continuation-in-part of application No. 10/135,317, filed on Apr. 30, 2002.

(51) Int. Cl.[7] .................................................. B08B 9/00
(52) U.S. Cl. ..................... 134/22.12; 423/477; 423/478; 210/749; 210/753; 210/754; 210/755; 210/756; 210/764; 422/28; 422/32; 166/311; 134/22.1; 134/22.11; 134/22.14; 134/22.16; 134/22.18; 134/22.19; 134/26; 134/28; 134/29; 134/34; 134/36; 134/41
(58) Field of Search .............................. 423/477, 478; 210/749, 753, 754, 755, 756, 764; 422/28, 32; 166/311; 134/22.1, 22.11, 22.12, 22.14, 22.16, 22.18, 22.19, 26, 28, 29, 34, 36, 41

(56) References Cited

U.S. PATENT DOCUMENTS

| | | | |
|---|---|---|---|
| 3,082,146 A | * 3/1963 | Wentworth et al. | 162/161 |
| 4,013,761 A | * 3/1977 | Ward et al. | 423/477 |
| 4,247,531 A | * 1/1981 | Hicks | 423/477 |
| 4,512,908 A | 4/1985 | Heile | 510/221 |
| 4,690,772 A | 9/1987 | Tell et al. | 510/161 |
| 4,929,365 A | 5/1990 | Clark et al. | 210/754 |
| 4,945,992 A | * 8/1990 | Sacco | 166/310 |
| 5,171,441 A | 12/1992 | Mason | 210/206 |
| 5,324,477 A | 6/1994 | Schroeder et al. | 422/32 |
| 5,401,419 A | 3/1995 | Kocib | 210/693 |
| 5,424,032 A | 6/1995 | Christensen et al. | 422/14 |
| 5,611,920 A | 3/1997 | Simpson et al. | 210/750 |
| 5,670,055 A | 9/1997 | Yu et al. | 210/698 |
| 5,676,920 A | * 10/1997 | Lipsztajn | 423/478 |
| 5,779,914 A | * 7/1998 | Brown et al. | 210/754 |
| 5,874,026 A | 2/1999 | Pilsits, Jr. et al. | 252/394 |
| 5,972,238 A | * 10/1999 | Rimpler et al. | 252/187.21 |
| 6,080,323 A | 6/2000 | Yu et al. | 210/758 |
| 6,123,966 A | * 9/2000 | Kross | 424/665 |
| 6,132,628 A | * 10/2000 | Barak | 210/756 |
| 6,139,830 A | 10/2000 | Donlan et al. | 424/78.09 |
| 6,183,649 B1 | * 2/2001 | Fontana | 210/699 |
| 6,215,008 B1 | 4/2001 | Heffron | 552/276 |
| 6,218,491 B1 | 4/2001 | Fu et al. | 526/271 |
| 6,379,539 B1 | * 4/2002 | Ubelhor | 210/104 |
| 2002/0014463 A1 | 2/2002 | Iverson et al. | 210/749 |
| 2004/0033190 A1 | * 2/2004 | Suty et al. | 423/477 |

FOREIGN PATENT DOCUMENTS

| | | |
|---|---|---|
| EP | 0 592 118 A1 | 4/1994 |
| GB | 2 313 369 A | 11/1997 |
| JP | 08013995 B2 | 4/1987 |
| KR | 8902542 B | 8/1986 |
| WO | WO 01/55717 A1 | 8/2001 |
| WO | WO 02/12130 A1 | 2/2002 |

OTHER PUBLICATIONS

"Alternative Disinfectants and Oxidants Guidance Manual", United States Environmental Protection Agency, Office of Water, EPA 815-R-99-014, Chapters 1–9, Appendix A–B, Apr. 1999.

"Control of Biofilm in Alkaline White Water Systems with Chlorine Dioxide", J.W. Wadsworth, G.D. Simpson, Ph.D., Engineering & Papermakers Conference, TAPPI Proceedings, pp. 1095–1102, 1997.

"Control of Legionella in Cooling Towers" Summary Guidelines, Section of Acute and Communicable Disease Epidemiology, Bureau of Community Health and Prevention, Division of Health, Wisconsin Department of Health and Social Services, T. Cullen, J. Torphy, I. Imm, J. Davis, M.D., pp. i–viii, 1–31, Appendix A—I, Aug. 1987.

"The Stability of Azoles to Chlorine and Chlorine Alternatives for Microbiological Control", M.T. Coschigano, W.S. Go, Drew Industrial Division Ashland Chemical, Inc., Boonton, New Jersey, pp. 375–379, IWC-93-63.

* cited by examiner

Primary Examiner—Sharidan Carrillo
(74) Attorney, Agent, or Firm—Michael B. Martin; Thomas M. Breininger

(57) ABSTRACT

On-Line and Off-Line methods of simultaneously cleaning and disinfecting an industrial water system are described and claimed. The methods involve the addition to the water of the industrial water system of a Compound selected from the group consisting of the alkali salts of chlorite and chlorate and mixtures thereof; and an acid, followed by allowing the water in the industrial water system to circulate for several hours. The reaction of the alkali salts of chlorite and chlorate and acid produces chlorine dioxide in-situ in the water of the industrial water system. The chlorine dioxide kills microorganisms and the acid acts to remove deposits upon the water-contact surfaces of the equipment. An alternative method involves the use of a chelating agent and a biocide. Other possible cleaning and disinfection reagents may be added as needed including corrosion inhibitors, chelating agents, biocides, surfactants and reducing agents. These cleaning and disinfecting methods work in a variety of industrial water systems including cooling water and boiler water systems.

8 Claims, No Drawings

METHODS OF SIMULTANEOUSLY CLEANING AND DISINFECTING INDUSTRIAL WATER SYSTEMS

CROSS-REFERENCE TO RELATED PATENT APPLICATION

This patent application is a continuation-in-part of U.S. patent application Ser. No. 10/135,317, filed Apr. 30, 2002, now pending.

FIELD OF THE INVENTION

This invention is in the field of industrial water systems. Specifically, this invention is in the field of cleaning and disinfection of industrial water systems.

BACKGROUND OF THE INVENTION

Throughout the world, there are many different types of industrial water systems. Industrial water systems exist so that necessary chemical, mechanical and biological processes can be conducted to reach the desired outcome. Fouling can occur even in industrial water systems treated with the best water treatment programs currently available. For purposes of this patent application "fouling" is defined as "the deposition of any organic or inorganic material on a surface".

If these industrial water systems are not periodically cleaned, then they will become heavily fouled. Fouling has a negative impact on the industrial water system. For example, severe mineral scale (inorganic material) will buildup on the water contact surfaces and anywhere there is scale, there is an ideal environment for the growth of microorganisms.

Evaporative cooling water systems are particularly prone to fouling. This fouling occurs by a variety of mechanisms including deposition of air-borne and water-borne and water-formed contaminants, water stagnation, process leaks, and other factors. If allowed to progress, the system can suffer from decreased operational efficiency, premature equipment failure, and increased health-related risks associated with microbial fouling.

Fouling can also occur due to microbiological contamination. Sources of microbial contamination in industrial water systems are numerous and may include, but are not limited to, air-borne contamination, water make-up, process leaks and improperly cleaned equipment. These microorganisms can establish microbial communities on any wetable or semi-wetable surface of the water system. Once these microbial populations are present in the bulk water more than 99% of the microbes present in the water will be present on all surfaces.

Exopolymeric substance secreted by microorganisms aid in the formation of biofilms as the microbial communities develop on the surface. These biofilms are complex ecosystems that establish a means for concentrating nutrients and offer protection for growth, and biofilms can accelerate scale, corrosion, and other fouling processes. Not only do biofilms contribute to reduction of system efficiencies, but they also provide an excellent environment for microbial proliferation that can include *Legionella* bacteria. It is therefore important that biofilms and other fouling processes be reduced to the greatest extent possible to minimize the health-related risk associated with *Legionella* and other water-borne pathogens.

There are several different cleaning or disinfection methods for cooling water systems. For example, mechanical cleaning, hyperhalogenation with and without surfactants or dispersants, and acid cleaning, are amongst the cleaning methods most commonly used.

A simple mechanical cleaning program consists of "power washing" and "scrubbing". Power washing refers to the use of high-pressure water directed at equipment surfaces such that the impact of the water on the surface removes deposits from those surfaces that can be reached. Mechanical cleaning strategies do not always remove all heavily adhering deposits such as deposited scale and biological slime from equipment surfaces. Further limitations on the use of mechanical cleaning include the fact that such methods are effective at removing only loose deposits, and not for removing deposits from within the fill (in the case of a cooling tower). For systems such as domestic water distribution pipes, power washing is completely ineffective. Mechanical cleaning methods also do not provide a means of disinfection, which is crucial to maintaining clean and safe equipment.

One standard procedure that uses hyperhalogenation and surfactant is commonly known as the "Wisconsin Protocol", see "CONTROL OF LEGIONELLA IN COOLING TOWERS", Summary Guidelines, Section of Acute and Communicable Disease Epidemiology, Bureau of Community Health and Prevention, Division of Health, Wisconsin Department of Health and Social Services, August 1987. The Wisconsin Protocol is used to disinfect an industrial water system following a Legionellosis outbreak. Even in the absence of an outbreak, hyperhalogenation is commonly used to reduce microbial fouling in water systems. Hyperhalogenation protocols do not remove mineral scale, thereby limiting their ability to remove or reduce biological foulants. In addition, the hyperhalogenation procedures that require a biodispersant have limited effectiveness within the period the protocol is implemented. The use of certain acids, such as sulfuric acid, in combination with high halogen doses, as specified in the Wisconsin Protocol, can form copper sulfate and other deposits that are subsequently difficult to remove. Finally, because the hyperhalogenation methods do not remove scale and other deposits sufficiently, microbial populations re-establish rapidly in the systems.

An "acid cleaning procedure" is designed to remove mineral scale. Acid is capable of removing alkaline scale from virtually all wetable surfaces. Acid cleaning procedures offer limited disinfection because of the lowered pH, but do not adequately penetrate biological deposits (biofilms) that remain associated with system surfaces.

Operators of industrial water systems use chlorine dioxide to kill microorganisms. Chlorine dioxide is a well-known biocide, but does not have the ability to remove mineral scale. Chlorine dioxide must be generated on-site where it is applied. There are several methods for generating and delivering chlorine dioxide. One of these methods uses acid in combination with sodium chlorite (acid activation). For example, the chlorine dioxide is generated using sodium chlorite and hydrochloric acid as follows:

$$5\ NaClO_2 + 4\ HCl = 4\ ClO_2 + 5\ NaCl + 2\ H_2O$$

Typically, the reactants (sodium chlorite and hydrochloric acid) are mixed and allowed to react to form chlorine dioxide. Following this reaction, the products (chlorine dioxide, sodium chloride, water, some remaining unreacted sodium chlorite, and hydrochloric acid) are added directly into the water of the industrial water system. Once this externally-generated chlorine dioxide solution is applied to the water system, the chlorine dioxide is diluted and either lost through volatility or is reduced by substances within the water system. Using this method, chlorine dioxide must be constantly generated outside the water system, and injected into the system to maintain a chlorine dioxide residual.

Patent Cooperation Treaty Patent Application WO 02/12130 A1 describes and claims a method of treating water in a water distribution system, comprising:

admixing a sodium chlorite solution with a second solution containing an acid to make a reacted mixture; and introducing a predetermined amount of the reacted mixture into a water system.

As described in this Patent Cooperation Treaty Patent Application, the preferred method of treating water includes the addition of a catalyst, wherein the catalyst is sodium molybdate.

United Kingdom Patent Application No. 2,313,369 describes and claims an aqueous composition having a pH of more than 9 consists of a stabilized chlorine dioxide precursor, an alkali metal polyphosphate and an alkali metal hydroxide. It also describes and claims a method of treating water in a water distribution system comprising the addition of an acid activator to the aqueous composition to reduce the pH to less than 7 and injecting the aqueous solution in to the water system.

It would be desirable to have a method for simultaneously cleaning and disinfecting an industrial water system.

SUMMARY OF THE INVENTION

The first aspect of the instant claimed invention is a method of simultaneously cleaning and disinfecting an industrial water system comprising the steps of:
a) providing an industrial water system;
b) adding to the water of said industrial water system
   i) a Compound, wherein said Compound is selected from the group consisting of the alkali salts of chlorite and chlorate, or a mixture thereof; and
   ii) an acid;
   wherein said acid is added before the Compound is added; and
c) allowing the water to circulate through the industrial water system for at least from about one to about 72 hours; and
d) draining the water from the industrial water system.

The second aspect of the instant claimed invention is a method of simultaneously cleaning and disinfecting an industrial water system comprising the steps of:
a) providing an industrial water system;
b) adding to the water of said industrial water system
   i) a Compound, wherein said Compound is selected from the group consisting of the alkali salts of chlorite and chlorate, or a mixture thereof; and
   ii) an acid;
   wherein said Compound is added before the acid is added; and
c) allowing the water to circulate through the industrial water system for at least from about one to about 72 hours; and
d) draining the water from the industrial water system.

The third aspect of the instant claimed invention is an on-line method of simultaneously cleaning and disinfecting an industrial water system comprising the steps of:
a) providing an industrial water system; wherein said industrial water system is selected from the group consisting of cooling water systems and boiler water systems;

b) optionally reducing the cycles of said industrial water system to single cycles and halting the feeding of the routine water maintenance chemicals to the water of the industrial water system;

c) adding a Compound selected from the group consisting of the alkali salts of chlorite and chlorate, or a mixture thereof, and optionally adding a corrosion inhibitor and optionally adding a dispersant to the water of said industrial water system; wherein enough Compound is added to reach a concentration of from about 1 ppm to about 1000 ppm; wherein if a corrosion inhibitor is added enough corrosion inhibitor is added to reach a concentration of from about 50 ppm to about 500 ppm and wherein if a dispersant is added enough dispersant is added to reach a concentration of from about 1 ppm to about 500 ppm;

d) lowering the pH of the water in the industrial water system to about 4.0 by adding an acid to the water of said industrial water system and maintaining the pH of the water in the industrial water system at about 4.0 for from about 1 to about 4 hours;

e) adding a chelating agent to the water of the industrial water system, wherein enough chelating agent is added to maintain the concentration of the chelating agent at from about 10 ppm to about 500 ppm in the water of the industrial water system; wherein said chelating agent is added either before or after the next step of raising the pH;

f) optionally raising the pH of the water in the industrial water system from about 5.5 to about 11 by either adding caustic or stopping the addition of acid or by a combination of both of these methods;

g) adding a biocide to the water of the industrial water system; wherein if the chelating agent is added after the optional step of raising the pH, then the chelating agent and the biocide from step g) may be added simultaneously to the water or the chelating agent may be added first followed by the biocide or the biocide may be added first, followed by the chelating agent; wherein the amount of biocide added is that amount sufficient to have a concentration of from about 1 ppm to about 500 ppm in the water of the industrial water system;

h) allowing the water in the industrial water system to circulate for an additional time period of from about 1 hour to about 120 hours; and i) concluding the cleaning and disinfecting method when the desired cleaning efficiency has been achieved; wherein, if feeding of the routine water treatment maintenance chemicals was stopped during the process, then now resuming the feeding of the routine water treatment maintenance chemicals to the water of the industrial water system; and wherein if feeding of the routine water treatment maintenance chemicals was not stopped during the procedure, then now bringing the industrial water system back to normal operation by stopping cleaning chemical feed, blowing down the water to reduce system cycles to a single cycle, and then proceeding under normal operating conditions.

The fourth aspect of the instant claimed invention is:
an on-line method of simultaneously cleaning and disinfecting an industrial water system comprising the steps of:
a) providing an industrial water system; wherein said industrial water system is selected from the group consisting of cooling water systems and boiler water systems;

b) optionally reducing the cycles of said industrial water system to single cycles and halting the feeding of the routine water maintenance chemicals to the water of the industrial water system.

c) adding a chelating agent to the water of the industrial water system, wherein enough chelating agent is added to maintain the concentration of the chelating agent at from about 10 ppm to about 500 ppm in the water of the industrial water system; wherein said chelating agent is added either before or after the optional next step of maintaining the pH;

d) optionally maintaining the pH of the water in the industrial water system from about 5.5 to about 11 by either adding caustic or stopping the addition of acid or by a combination of both of these methods;

e) adding a biocide to the water of the industrial water system; wherein if the chelating agent is added after the optional step of maintaining the pH, then the chelating agent and the biocide from step e) may be added simultaneously to the water or the chelating agent may be added first followed by the biocide or the biocide may be added first, followed by the chelating agent; wherein the amount of biocide added is that amount sufficient to have a concentration of from about 1 ppm to about 500 ppm in the water of the industrial water system;

f) allowing the water in the industrial water system to circulate for an additional time period of from about 1 hour to about 120 hours; and g) concluding the cleaning and disinfecting method when the desired cleaning efficiency has been achieved; wherein, if feeding of the routine water treatment maintenance chemicals was stopped during the process, then now resuming the feeding of the routine water treatment maintenance chemicals to the water of the industrial water system; and wherein if feeding of the routine water treatment maintenance chemicals was not stopped during the procedure, then now bringing the industrial water system back to normal operation by stopping cleaning chemical feed, blowing down the water to reduce system cycles to a single cycle, and then proceeding under normal operating conditions.

DETAILED DESCRIPTION OF THE INVENTION

Throughout this patent application, the following terms have the stated meaning

"Fouling" refers to the deposition of any organic or inorganic material on a surface. These deposits impede water flow and/or heat transfer, and harbor microorganisms that cause increased deposition, enhance corrosion and increase health-related risks.

"Cleaning" means reducing the overall quantity of deposits, which is desirable because reducing the overall quantity of deposits improves the overall efficiency of the industrial water system.

"Disinfection" is typically used to describe a method for killing microorganisms. As used herein, the goal of disinfection is to cause an overall significant reduction in the number or viability of microorganisms within the water system.

"ONC" refers to Ondeo Nalco Company, Ondeo Nalco Center, 1601 W. Diehl Road, Naperville, Ill. 60563, telephone (630) 305–1000.

The first and second aspects of the instant claimed invention are a method of simultaneously cleaning and disinfecting an industrial water system comprising the steps of:

a) providing an industrial water system;

b) adding to the water of said industrial water system
   i) a Compound selected from the group consisting of the alkali salts of chlorite and chlorate or a mixture thereof; and
   ii) an acid; and
   wherein said acid is added before the Compound is added, or the acid is added after the Compound is added;

c) allowing the water to circulate through the industrial water system for at least from about one to about 72 hours; and d) draining the water from the industrial water system.

The method of the instant claimed invention can be used to simultaneously clean and disinfect industrial water systems that are being installed, those that are currently in operation, are temporarily not operating, or have been inactive for extended periods and are being restored to service.

The method of the instant claimed invention can be used to clean and disinfect many industrial water systems. These industrial water systems include, but are not limited to cooling water systems, including open recirculating, closed and once-through cooling water systems; boilers and boiler water systems; petroleum wells, downhole formations, geothermal wells and other oil field applications; mineral process waters including mineral washing, flotation and benefaction; paper mill digesters, washers, bleach plants, stock chests, and white water systems, and paper machine surfaces; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation systems, water purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment, municipal water systems, potable water systems, aquifers, water tanks, sprinkler systems and water heaters. The preferred industrial water systems to be simultaneously cleaned and disinfected by the method of the instant claimed invention are cooling water systems, including open recirculating, closed and once-through cooling water systems, paper machine surfaces, food processing streams, waste treatment systems and potable water systems. The most preferred industrial water systems to be simultaneously cleaned and disinfected by the method of the instant claimed invention are cooling water systems, including open recirculating, closed and once-through cooling water systems.

Prior to conducting the method of the instant claimed invention it is typically recommended, though not required, that the addition of any chemical or biological treatment chemicals to the water be discontinued. It is also recommended to stop all energy transfer within the system so that prior to addition of the Compound and acid, the water of the industrial water system is circulating through the industrial water system without being chemically or biologically treated and without having heat transfer occurring.

The Compound is selected from the alkali salts of chlorite and chlorate and mixtures thereof. These alkali salts include sodium chlorite, potassium chlorite, sodium chlorate and potassium chlorate. The preferred alkali salts are sodium chlorite and sodium chlorate. The most preferred alkali salt is sodium chlorite.

The alkali salts of chlorite and chlorate are commodity chemicals that can be obtained from most chemical supply companies. Sodium chlorite can be obtained either at its normal pH or in its colloquially referred to "stabilized form" at an elevated pH. The preferred sodium chlorite is a 25% solution of sodium chlorite in water. This material is available as HYG-25 from ONC.

Sodium chlorate is a commodity chemical that can be obtained from most chemical supply companies. The preferred sodium chlorate is from about a 20 to about a 50 Wt/Wt % solution of sodium chlorate in water. This preferred sodium chlorate is available from Eka Chemicals, Inc., 1775 West Oak Commons Court, Marietta, Ga. 30062-2254 USA, telephone number 1-770-578-0858.

Potassium chlorite and potassium chlorate are both available from most chemical supply companies.

The amount of sodium chlorite or potassium chlorite added to the water of the industrial water system depends upon what type of industrial water system is being cleaned and disinfected. If the method of the instant claimed invention is applied to a cooling water system, then the amount of sodium chlorite or potassium chlorite added is from about 1 ppm to about 1000 ppm, preferably from about 10 ppm to about 500 ppm and most preferably from about 50 ppm to about 250 ppm.

The amount of sodium chlorate or potassium chlorate added to the water of the industrial water system depends upon what type of industrial water system is being cleaned and disinfected. If the method of the instant claimed invention is applied to a cooling water system, then the amount of sodium chlorate added is from about 1 ppm to about 1000 ppm, preferably from about 10 ppm to about 500 ppm and most preferably from about 50 ppm to about 250 ppm.

If sodium chlorite or potassium chlorite and sodium chlorate or potassium chlorate are both used then the ratio of chlorite to chlorate, expressed in weight percent, is from about 1:99 to about 99:1, preferably from about 10:90 to about 90:10, and most preferably about 50:50. The total amount of both chlorite and chlorate together is the same as that for either chlorite or chlorate used separately.

The acid is selected from the group consisting of mineral acids and organic acids wherein said mineral acids are selected from the group consisting of hydrochloric acid, sulfuric acid, amido sulfuric acid (98%), nitric acid, phosphoric acid, hydrofluoric acid and sulfamic acid; and said organic acids are selected from the group consisting of citric acid and its salts, formic acid, acetic acid, peracids including peracetic acid, peroxyacetic acid and peroxyformic acid, glycolic acid (hydroxyacetic acid), oxalic acid, propionic acid, lactic acid (hydroxypropionic acid) and butyric acid. The choice of acid depends primarily upon metallurgy within the system. For metals such as carbon steel, copper or yellow metal alloys the preferred acids are hydrochloric acid, sulfamic acid, formic acid and glycolic acid. The most preferred acid, for most metals, is hydrochloric acid.

These acids are commercial chemicals available from a chemical supply company. These acids can be purchased in dry or in liquid form or in formulations that contain other functional chemicals which also can be in dry or liquid form. For instance, most of these acids can be obtained in formulation with corrosion inhibitors. Hydrochloric acid formulated with a corrosion inhibitor made of diethyl urea is sold as Nalco®2560 Inhibited HCl by ONC.

The amount of acid added to the water of the industrial water system depends upon what type of industrial water system is being cleaned and disinfected. If the method of the instant claimed invention is applied to a cooling water system, then the amount of acid added is that required to achieve and maintain a pH from about 1 to about 5, preferably from about 1 to about 3 and most preferably from about 2 to about 2.5. People of ordinary skill in the art know how to calculate how much of each acid would be required in order to achieve the desired pH by taking into account the system volume and the alkalinity within the system.

The Compound that is selected from the group consisting of the alkali salts of chlorite and chlorate and mixtures thereof and the acid are added directly to the water of the industrial water system, without being premixed prior to addition. Either the acid is added before the Compound or the Compound is added before the acid. It is possible, although not preferred, to add the acid and Compound simultaneously to the water.

The advantage of the instant claimed method is that it is possible to obtain continuous generation of chlorine dioxide disinfectant throughout the water system while also achieving simultaneous acid cleaning. Adding the Compound and the acid separately allows a certain amount of circulation of the Compound and acid prior to their reaction to create chlorine dioxide. This means more chlorine dioxide is created farther away from the point of addition of the Compound and the acid.

After the Compound and acid are added to the water, the water is allowed to circulate throughout the industrial water system. This circulation of water allows the cleaning and disinfection of the "water-contact" surfaces of equipment in the industrial water system. In addition to the cleaning and disinfection of the water contact surfaces, volatile chlorine dioxide is also capable of reaching surfaces that are not continuously in contact with water.

The water in the industrial water system is allowed to circulate for a time period of from about 1 hour to about 72 hours, preferably from about 1 hour to about 24 hours and most preferably from about 1 hour to about 8 hours.

During these time periods it is possible, though not required, to monitor the progress of the cleaning and {indirectly monitor} disinfection by using standard techniques to determine the amount of ions present in the water due to the breaking up and detachment of inorganic deposits. The inorganic deposits are typically calcium salts, magnesium salts, iron oxide, copper oxide and manganese salts. For instance, it is known that it is typical for the amount of calcium ion in the water to rise steadily as the cleaning progresses and scale, known to contain calcium, is detached from the surfaces of the equipment. When the amount of calcium in the water plateaus it indicates that the cleaning is complete because no new calcium scale is being dissolved.

After the cleaning and disinfection is finished, the water in the industrial water system must be drained and sent for appropriate treatment so that it can be discharged in compliance with state and local regulations. Of course, once the water is drained, it may be necessary to conduct additional mechanical cleaning of the water contact surfaces. This mechanical cleaning is recommended when the cleaning and disinfection has worked so well that there is an accumulation of loose dirt and other undesired material collected in the nooks and crannys of the industrial water system. These nooks and crannys can include the fill used in most cooling towers. After mechanical cleaning is over, it is possible to refill the water and begin operation of the industrial water system. For heavily contaminated industrial water systems it is also possible to fill the industrial water system with water and conduct the method of the instant claimed invention again.

In addition to the chemicals named, it is possible to conduct the method of the instant claimed invention by adding additional functional chemicals. These additional functional chemicals include additional biocides, corrosion inhibitors, dispersants, surfactants, reducing agents and chemicals added for pH adjustment.

Additional biocides can be added when microbial contamination is severe. Biocides suitable for use in the instant claimed invention are selected from the group consisting of oxidizing or non-oxidizing biocides. Oxidizing biocides include, but are not limited to, chlorine bleach, chlorine, bromine and materials capable of releasing chlorine and bromine. The preferred oxidizing biocide is chlorine bleach. Non-oxidizing biocides include, but are not limited to, glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, didecyl dimethyl ammonium chloride, poly(oxyethylene (dimethyliminio)ethylene(dimethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis (tributyltin)oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 4,5-dichloro-2-n-octyl-4-isothiazoline-3-one, 5-chloro-2-methyl-4-isothiazolin-3-one and 2-methyl-4-isothiazolin-3-one. The preferred non-oxidizing biocide is 2,2-dibromo-3-nitrilopropionamide and is available from ONC.

If the method of the instant claimed invention is applied to a cooling water system, then the amount of oxidizing biocide added is from about 0.1 ppm to about 200 ppm, preferably from about 1 ppm to about 100 ppm, more preferably from about 5 to about 50 ppm and most preferably from about 5 ppm to about 20 ppm.

Corrosion inhibitors can be added when needed to reduce corrosion of the metal in the industrial water system. Corrosion inhibitors for multi-metal protection are typically triazoles, such as, but not limited to, benzotriazole, halogenated triazoles, nitro-substituted azoles, and other triazoles as listed in U.S. Pat. No. 5,874,026, which is incorporated by reference in its entirety. The preferred triazole is benzotriazole.

Triazoles are commercially available from most chemical supply companies. The preferred benzotriazole is Nalco® 73199, which is available from Ondeo Nalco Company.

Whether a corrosion inhibitor is used depends upon the industrial water system and the composition of the water contact surfaces in the industrial water system. For example, if all the water contact surfaces in the industrial water system are wood, noble metals, glass, titanium or plastic, then the use of corrosion inhibitor in those systems is not indicated. However, when the water contact surfaces are non-titanium metal, such as, but not limited to, stainless steel, carbon steel, galvanized steel, and yellow metals such as copper, admiralty and brass, then the use of a corrosion inhibitor is preferred.

The amount of corrosion inhibitor added to the water of the industrial water system depends upon what type of industrial water system is being cleaned and disinfected. If the method of the instant claimed invention is applied to a cooling water system, then the amount of corrosion inhibitor added is from about 1 ppm to about 2000 ppm, preferably from about 10 ppm to about 1000 ppm and most preferably from about 50 ppm to about 600 ppm.

The corrosion inhibitor may be added before, after or during the addition of the Compound and the acid. The corrosion inhibitor is preferably added prior to the addition of acid. The corrosion inhibitor can be added immediately before the acid and Compound are added. However, it is preferred that the corrosion inhibitor be added sufficiently in advance of the addition of acid that the corrosion inhibitor can circulate throughout the system. Thus it is preferred that the corrosion inhibitor be added from about 1 hour to about 24 hours prior to addition of the Compound and acid.

The corrosion inhibitor could also be preformulated with other ingredients being added to the water. As mentioned previously, corrosion inhibitor can be formulated with acid to create an "inhibited acid".

Dispersants are added when needed to keep particulate matter present in the water of an industrial water system dispersed, so that it does not agglomerate and cause fouling during the cleaning and disinfecting process. Dispersants are typically low molecular weight anionic polymers, with "low" referring to a weight average molecular weight of from about 500 to about 20,000. These polymers are typically, but not limited to acrylic acid, polymaleic acid, copolymers of acrylic acid with sulfonated monomers and alkyl esters thereof. These polymers can include terpolymers of acrylic acid, acrylamide and sulfonated monomers. These polymers can also include quad-polymers consisting of acrylic acid and three other monomers.

Dispersant polymers are commercially available from most chemical supply companies. The preferred dispersant polymer is a High Stress Polymer such as High Stress Polymer PR 4832 which is available from Ondeo Nalco Company.

Whether a dispersant is used depends upon the industrial water system, the deposits present in the system and the foulants present in the water and the composition of the water contact surfaces in the industrial water system.

The amount of dispersant added to the water of the industrial water system depends upon what type of industrial water system is being cleaned and disinfected. If the method of the instant claimed invention is applied to a cooling water system then the amount of dispersant added is from about 1 ppm to about 500 ppm, preferably from about 5 ppm to about 200 ppm and most preferably from about 10 ppm to about 100 ppm.

The dispersant may be added before, after or during the addition of the Compound and the acid. The dispersant could also be preformulated with other ingredients being added to the water.

One or more surfactants may be added when and where needed to enhance the cleaning and disinfection process. Surfactants useful in industrial water systems include, but are not limited to, ethylene oxide propylene oxide copolymers, linear alkylbenzene sulfonates ("LAS"), ethoxylated phosphate esters, and alkyl polyglycosides, and other surfactants described in U.S. Pat. No. 6,139,830, U.S. Pat. No. 5,670,055 and U.S. Pat. No. 6,080,323, which are all incorporated by reference.

Surfactants are commercially available from most chemical supply companies. The preferred surfactants are ethylene oxide propylene oxide copolymers and alkyl polyglycosides. These surfactants CL-103, CL-361, CL-362, Nalco®73550, and Nalco®7348 are available from ONC.

Whether a surfactant is used depends upon the industrial water system, the deposit or foulant, and the composition of the water contact surfaces in the industrial water system.

The amount of surfactant added to the water of the industrial water system depends upon what type of industrial water system is being cleaned and disinfected. If the method of the instant claimed invention is applied to a cooling water system, then the amount of surfactant added is from about 0.1 ppm to about 1000 ppm, preferably from about 1 ppm to about 500 ppm and most preferably from about 5 ppm to about 100 ppm.

Surfactant could be added at any time during the method of simultaneous cleaning and disinfection, but surfactant would preferably be added after chlorine dioxide generation has started {in order to reduce any potential aerosolization of viable microbial foulants}.

One or more reducing agents may be added when and where needed to react with oxidants present in order to prepare the water for discharge in compliance with state and local environmental regulations. Reducing agents suitable for use in the method of the instant claimed invention include, but are not limited to, sodium thiosulfate, sodium bisulfite, sodium metabisulfite and sodium sulfite.

Reducing agents such as these are commercially available from most chemical supply companies. The preferred reducing agent is sodium bisulfite which is available from Ondeo Nalco Company.

Whether a reducing agent is used depends upon the industrial water system and the amount of oxidants present therein. The amount of reducing agent added to the water of the industrial water system depends upon what type of industrial water system is being cleaned and disinfected. If the method of the instant claimed invention is applied to a cooling water system, then the amount of reducing agent added is equimolar to the amount of oxidant present. Another way of determining the amount of reducing agent that is required is to add reducing agent until there is no residual halogen present.

The reducing agent is typically added at the conclusion of the cleaning and disinfection process just before the water is to be discharged or may be added to the discharge pipe or reservoir.

A pH adjusting chemical may be added when needed to adjust the pH of the water being discharged from the industrial water system. Typical pH adjusting chemicals include, but are not limited to, NaOH (aka "caustic"), KOH, $Ca(OH)_2$, $Na_2CO_3$ and $K_2CO_3$. The preferred pH adjusting chemical is caustic, specifically a 50% solution of NaOH in water. Caustic is commercially available from most chemical supply companies.

The amount of pH adjusting chemical added to the water of the industrial water system depends upon what type of industrial water system is being cleaned and disinfected, what the pH of the water typically is and what are the pH requirements for the water being discharged from the industrial water system.

If the method of the instant claimed invention is applied to a cooling water system, then the amount of pH adjusting chemical added is that required to achieve a pH from about 2 to about 8, preferably from about 3 to about 7 and most preferably from about 4 to about 6. The pH adjusting chemical is typically added at the conclusion of the cleaning and disinfection process just before the water is to be discharged or it may be added to the discharge pipe or reservoir.

In practicing the method of the instant claimed invention all of the chemicals may be added separately. Aside from the Compound and acid being added separately, the other chemicals may be formulated together.

A preferred formulation would include corrosion inhibitor, dispersant and surfactant blended together in a single product.

At the conclusion of the process, the water containing the cleaning and disinfection chemicals and residual material removed from the water is drained from the industrial water system. Then, the system can be refilled with water and returned to service right away or not, depending on the needs of the system operators. It is of course possible to fill the tower with fresh water and conduct the method of the instant claimed invention again, in order to clean heavily contaminated industrial water systems.

If a cooling tower has been cleaned and disinfected by the method of the instant claimed invention, any of the following actions can take place at the conclusion of the method.

1) fill the cooling tower using fresh make-up water, and begin dosing a "normal" treatment program of inhibitors and biocides;
2) fill the cooling tower using fresh make-up water, and begin dosing a program of inhibitors and/or biocides at elevated doses, to achieve passivation of any exposed metals and kill off any remaining organisms, followed by resumption of a "normal" treatment program;
3) leave the cooling tower dry during a period in which cooling is not required; or fill the system with fresh make-up water, and slug dose inhibitors and/or biocide at elevated doses, then drain the system (without ever having resumed normal function) and leave dry during a period in which cooling is not required.
4) fill the cooling tower with fresh make-up water, drain the system and refill, slug dose inhibitors and/or biocide at elevated or normal doses, then return to service.

The advantages of the first and second aspects of the instant claimed invention include the fact that this cleaning and disinfection procedure removes deposits from virtually all wetable surfaces, and simultaneously disinfects bulk water and all wetable surfaces, and some surfaces not continually in contact with the water, by in-situ generation of $ClO_2$. The method of the instant claimed invention is designed to minimize corrosion while cleaning and disinfection are taking place, can be completed in less than eight hours, effectively removes microbial deposits and significantly extends the period for microbial re-colonization. The procedure works well to clean heavily fouled industrial water systems.

The third aspect of the instant claimed invention is an on-line method of simultaneously cleaning and disinfecting an industrial water system comprising the steps of:

a) providing an industrial water system; wherein said industrial water system is selected from the group consisting of cooling water systems and boiler water systems;
b) optionally reducing the cycles of said industrial water system to single cycles and halting the feeding of the routine water maintenance chemicals to the water of the industrial water system;
c) adding a Compound selected from the group consisting of the alkali salts of chlorite and chlorate, or a mixture thereof, and optionally adding a corrosion inhibitor and optionally adding a dispersant to the water of said industrial water system; wherein enough Compound is added to reach a concentration of from about 1 ppm to about 1000 ppm; wherein if a corrosion inhibitor is added enough corrosion inhibitor is added to reach a concentration of from about 50 ppm to about 500 ppm and wherein if a dispersant is added enough dispersant is added to reach a concentration of from about 1 ppm to about 500 ppm;

d) lowering the pH of the water in the industrial water system to about 4.0 by adding an acid to the water of said industrial water system and maintaining the pH of the water in the industrial water system at about 4.0 for from about 1 to about 4 hours;

e) adding a chelating agent to the water of the industrial water system, wherein enough chelating agent is added to maintain the concentration of the chelating agent at from about 10 ppm to about 500 ppm in the water of the industrial water system; wherein said chelating agent is added either before or after the next step of raising the pH;

f) optionally raising the pH of the water in the industrial water system from about 5.5 to about 11 by either adding caustic or stopping the addition of acid or by a combination of both of these methods;

g) adding a biocide to the water of the industrial water system; wherein if the chelating agent is added after the step of raising the pH, then the chelating agent and the biocide from step g) may be added simultaneously to the water or the chelating agent may be added first followed by the biocide or the biocide may be added first, followed by the chelating agent; wherein the amount of biocide added is that amount sufficient to have a concentration of from about 1 ppm to about 500 ppm in the water of the industrial water system;

h) allowing the water in the industrial water system to circulate for an additional time period of from about 1 hour to about 120 hours; and i) concluding the cleaning and disinfecting method when the desired cleaning efficiency has been achieved; wherein, if feeding of the routine water treatment maintenance chemicals was stopped during the process, then now resuming the feeding of the routine water treatment maintenance chemicals to the water of the industrial water system; and wherein if feeding of the routine water treatment maintenance chemicals was not stopped during the procedure, then now bringing the industrial water system back to normal operation by stopping the cleaning chemical feed, blowing down the water to reduce system cycles to a single cycle, and then proceeding under normal operating conditions.

The third aspect of the instant claimed invention is a method applicable to cooling water systems and boiler water systems. These industrial water systems consist of evaporative cooling towers, open re-circulating, closed and once-through cooling water systems; boilers and boiler water systems and industrial water systems including cooling water equipment and boiler equipment.

The Compound is selected from the alkali salts of chlorite and chlorate and mixtures thereof. These alkali salts include sodium chlorite, potassium chlorite, sodium chlorate and potassium chlorate. The preferred alkali salts are sodium chlorite and sodium chlorate. The most preferred alkali salt is sodium chlorite.

The alkali salts of chlorite and chlorate are commodity chemicals that can be obtained from most chemical supply companies. Sodium chlorite can be obtained either at its normal pH or in its colloquially referred to "stabilized form" at an elevated pH. The preferred sodium chlorite is a 25% solution of sodium chlorite in water. This material is available as HYG-25 from ONC.

Sodium chlorate is a commodity chemical that can be obtained from most chemical supply companies. The preferred sodium chlorate is from about a 20 to about a 50 Wt/Wt % solution of sodium chlorate in water. This preferred sodium chlorate is available from Eka Chemicals, Inc., 1775 West Oak Commons Court, Marietta, Ga. 30062-2254 USA, telephone number 1-770-578-0858.

Potassium chlorite and potassium chlorate are both available from most chemical supply companies.

The amount of sodium chlorite or potassium chlorite added to the water of the industrial water system depends upon what type of industrial water system is being cleaned and disinfected. If the method of the instant claimed invention is applied to a cooling water system, then the amount of sodium chlorite or potassium chlorite added is from about 1 ppm to about 1000 ppm, preferably from about 10 ppm to about 500 ppm, most preferably from about 50 ppm to about 250 ppm and most highly preferably about 100 ppm.

If sodium chlorite or potassium chlorite and sodium chlorate or potassium chlorate are both used then the ratio of chlorite to chlorate, expressed in weight percent, is from about 1:99 to about 99:1, preferably from about 10:90 to about 90:10, and most preferably about 50:50. The total amount of both chlorite and chlorate together is the same as that for either chlorite or chlorate used separately.

The corrosion inhibitor optionally used in the third aspect of the instant claimed invention is selected from the group consisting of benzotriazole, halogenated triazoles, nitro-substituted azole, and the triazoles listed in U.S. Pat. No. 5,874,026, which is incorporated by reference in its entirety. The preferred triazole is benzotriazole. Benzotriazole is available from ONC as Nalco 73199. The amount of azole added is that amount sufficient to reach a concentration of about 50 to about 500 ppm in the water of the industrial water system. The preferred concentration of azole is about 100 ppm in the water of the industrial water system.

The dispersant optionally used in the third aspect of the instant claimed invention is selected from the group consisting of, but not limited to, High Stress Polymer (as previously described), acrylic acid, polymaleic acid, copolymers of acrylic acid with sulfonated monomers and alkyl esters thereof. These polymeric dispersants can include terpolymers of acrylic acid, acrylamide and sulfonated monomers. These polymeric dispersants can also include quad-polymers consisting of acrylic acid and three other monomers. The preferred dispersant is a terpolymer comprising from about 30–70 mol % acrylic acid, from about 10–30 mol % Acrylamide and from about 20–40 mol % aminomethylsulfonic acid. A terpolymer with such composition is available from ONC as High Stress Polymer PR 4382.

The amount of dispersant added is that amount sufficient to reach a concentration of from about 1 ppm to about 500 ppm. The preferred amount of dispersant is about 100 ppm.

The acid used in the third aspect of the instant claimed invention is either a mineral acid or an organic acid selected from the group consisting of hydrochloric acid, sulfuric acid, amido sulfuric acid (98%), nitric acid, phosphoric acid, hydrofluoric acid and sulfamic acid; and said organic acids are selected from the group consisting of citric acid and its salts, formic acid, acetic acid, peracids including peracetic acid, peroxyacetic acid and peroxyformic acid, glycolic acid (hydroxyacetic acid), oxalic acid, propionic acid, lactic acid (hydroxypropionic acid) and butyric acid. The preferred acid is glycolic acid, which is available as Nalco R3076 from ONC. The amount of acid added is that amount sufficient to lower the pH of the water to about 4.0 and subsequently to maintain the pH at about 4.0.

The chelating agent useful in the third aspect of the instant claimed invention is selected from the group consisting of sodium hexametaphosphate, sodium polyphosphate, phosphonates, and polycarboxylates (homopolymers and copolymers). The preferred chelating agent is sodium hexametaphosphate. It is available as Glassy Calgon from ONC. Sufficient chelating agent is added such that the concentration of the chelating agent at from about 10 ppm to about 500 ppm in the water of the industrial water system.

The biocide useful in the third aspect of the instant claimed invention can be an oxidizing biocide or a non-oxidizing biocide. Oxidizing biocides are selected from the group consisting of chlorine bleach, chlorine, bromine and materials capable of releasing chlorine and bromine. The preferred oxidizing biocide is chlorine bleach. Non-oxidizing biocides are selected from the group consisting of glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, didecyl dimethyl ammonium chloride, poly(oxyethylene (dimethyliminio)ethylene(dimethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis(tributyltin)oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 4,5-dichloro-2-n-octyl-4-isothiazoline-3-one, 5-chloro-2-methyl-4-isothiazolin-3-one and 2-methyl-4-isothiazolin-3-one, The preferred non-oxidizing biocide is 2,2-dibromo-3-nitrilopropionamide, which is available as Nalco N7649 from ONC. The amount of biocide added is that amount sufficient to have a concentration of from about 1 ppm to about 20 ppm in the water of the industrial water system.

In the third aspect of the instant claimed invention, the on-line method of cleaning and disinfection of industrial water systems allows for cleaning of inorganic and organic deposits initially through lowered pH, using an acid for a short period of time and subsequently for a prolonged period of time using a chelating agent at a near neutral pH. The disinfection takes place initially through the in-situ generation of chlorine dioxide when the pH is about 4.0, followed by addition of a chelating agent and a biocide when the pH is near neutral.

The fourth aspect of the instant claimed invention is: an on-line method of simultaneously cleaning and disinfecting an industrial water system comprising the steps of:

a) providing an industrial water system; wherein said industrial water system is selected from the group consisting of cooling water systems and boiler water systems;

b) optionally reducing the cycles of said industrial water system to single cycles and halting the feeding of the routine water maintenance chemicals to the water of the industrial water system.

c) adding a chelating agent to the water of the industrial water system, wherein enough chelating agent is added to maintain the concentration of the chelating agent at from about 10 ppm to about 500 ppm in the water of the industrial water system; wherein said chelating agent is added either before or after the optional next step of maintaining the pH;

d) optionally maintaining the pH of the water in the industrial water system from about 5.5 to about 11 by either adding caustic or stopping the addition of acid or by a combination of both of these methods;

e) adding a biocide to the water of the industrial water system; wherein if the chelating agent is added after the optional step of maintaining the pH, then the chelating agent and the biocide from step e) may be added simultaneously to the water or the chelating agent may be added first followed by the biocide or the biocide may be added first, followed by the chelating agent; wherein the amount of biocide added is that amount sufficient to have a concentration of from about 1 ppm to about 500 ppm in the water of the industrial water system;

f) allowing the water in the industrial water system to circulate for an additional time period of from about 1 hour to about 120 hours; and g) concluding the cleaning and disinfecting method when the desired cleaning efficiency has been achieved; wherein, if feeding of the routine water treatment maintenance chemicals was stopped during the process, then now resuming the feeding of the routine water treatment maintenance chemicals to the water of the industrial water system; and wherein if feeding of the routine water treatment maintenance chemicals was not stopped during the procedure, then now bringing the industrial water system back to normal operation by stopping cleaning chemical feed, blowing down the water to reduce system cycles to a single cycle, and then proceeding under normal operating conditions.

In the fourth aspect of the instant claimed invention, cleaning is attributed to chelation by the chelating agent and the disinfection occurs as a function of the added biocide.

The chelating agent useful in the fourth aspect of the instant claimed invention is selected from the group consisting of sodium hexametaphosphate, sodium polyphosphate, phosphonates, and polycarboxylates (homopolymers and copolymers). The preferred chelating agent is sodium hexametaphosphate. It is available as Glassy Calgon from ONC. Sufficient chelating agent is added such that the concentration of the chelating agent at from about 10 ppm to about 500 ppm in the water of the industrial water system.

The biocide useful in the fourth aspect of the instant claimed invention can be an oxidizing biocide or a non-oxidizing biocide. Oxidizing biocides are selected from the group consisting of chlorine bleach, chlorine, bromine and materials capable of releasing chlorine and bromine. The preferred oxidizing biocide is chlorine bleach.

Non-oxidizing biocides are selected from the group consisting of glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, didecyl dimethyl ammonium chloride, poly(oxyethylene (dimethyliminio)ethylene(dimethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis (tributyltin)oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 4,5-dichloro-2-n-octyl-4-isothiazoline-3-one, 5-chloro-2-methyl-4-isothiazolin-3-one and 2-methyl-4-isothiazolin-3-one, The preferred non-oxidizing biocide is 2,2-dibromo-3-nitrilopropionamide, which is available as Nalco N7649 from ONC. The amount of biocide added is that amount sufficient to have a concentration of from about 1 ppm to about 500 ppm in the water of the industrial water system.

The following examples are presented to be illustrative of the present invention and to teach one of ordinary skill how to make and use the invention. These examples are not intended to limit the invention or its protection in any way.

EXAMPLES

A plastic Pilot Cooling Tower with titanium metal heat exchangers and a plastic sump is chosen as a test site for the method of the second aspect of the instant claimed invention. The Pilot Cooling Tower is in almost continuous use for over one year so there is severe contamination present. The contamination is believed to be both inorganic scale as well as microbiological sessile populations. There is visible fouling on most of the water contact surfaces as well as visible particulate matter present in the water that is circulating.

To conduct the method of the instant claimed invention it is necessary to take the Pilot Cooling Tower out of service for 24 hours.

To prepare for the cleaning and disinfection of the Pilot Cooling Tower, the cooling system heat load is removed. The cooling system fans are turned-off and the blowdown valve is closed. The addition of water treatment program chemicals are discontinued, such that the water circulating through the Pilot Cooling Tower has only residual water treatment chemicals present.

Throughout the cleaning and disinfection program, Pilot Cooling Tower water recirculation remains on. Benzotriazole and the dispersant, which is High Stress Polymer PR 4832 from ONC are added to the water of the Pilot Cooling Tower. Enough benzotriazole is added to achieve a concentration of about 100 ppm. Enough High Stress Polymer is added to achieve a concentration of about 100 ppm.

Sufficient sodium chlorite ($NaClO_2$), taken from the chemical stockroom, is added to the system water such that its concentration in the water is 100 ppm. The sodium chlorite is circulated in the system for 30 minutes.

Inhibited hydrochloric acid is then added to the water. Sufficient hydrochloric acid is added such that the pH of the water is from about 2.0 to about 3.0, preferably about 2.5. The water is circulated for 6 hours while continuing to add whatever acid is required in order to maintain a pH of from about 2.0 to about 2.5. During cleaning and disinfection, samples are periodically collected and monitored for chlorine dioxide using standard analytical technique to determine chlorine dioxide {such as the diethyl-p-phenylene diamine test ("the DPD test") for free residual chlorine dioxide, expressed "as chlorine"} as well as determining the level of hardness present by complexometric titration.

During this six hour time period, chlorine dioxide concentrations are found to be in the range of from about 0.5 to about 1.0 ppm, expressed as free chlorine. Hardness values increase from 600 to 2000 ppm over a 5 hour period. After 5 hours, the hardness value increases are minimal and acid addition is stopped. The system water is recirculated for one additional hour. The system is drained. The system is flushed with fresh makeup water and drained a second time.

A visual inspection of the water contact surfaces shows clean surfaces with no contamination. The method of simultaneous cleaning and disinfection is deemed to be a success.

After the second drainage, the Pilot Cooling Tower is refilled with fresh makeup water and returned to normal service.

Example 2

This is an example of the third aspect of the instant claimed invention.

A plastic Pilot Cooling Tower with titanium metal heat exchangers and a plastic sump is chosen as a test site for the method of the third aspect of the instant claimed invention. The Pilot Cooling Tower is in almost continuous use so there is severe contamination present. The contamination is believed to be both inorganic scale as well as microbiological sessile populations. There is visible fouling on most of the water contact surfaces as well as visible particulate matter present in the water that is circulating.

To prepare for the cleaning and disinfection of the Pilot Cooling Tower, the cooling system water is blown-down to reduce system water to single cycle. The heat load and the cooling system fans is maintained in operation. For this example, the addition of water treatment program chemicals is discontinued, such that the water circulating through the Pilot Cooling Tower has only residual water treatment chemicals present.

Throughout the cleaning and disinfection program, Pilot Cooling Tower water re-circulation remains on. Benzotriazole and the dispersant, which is High Stress Polymer PR 4832 from ONC are added to the water of the Pilot Cooling Tower. Enough benzotriazole is added to achieve a concentration of about 100 ppm. Enough High Stress Polymer is added to achieve a concentration of about 100 ppm.

Sufficient sodium chlorite ($NaClO_2$), taken from the chemical stockroom, is added to the system water such that its concentration in the water is 100 ppm. The sodium chlorite is circulated in the system for 30 minutes.

Glycolic acid is then added to the water. Sufficient glycolic acid is added such that the pH of the water is from about 3.5 to about 5.5, preferably about 4.0. The water is circulated for about 1.0 to about 4.0 hours, preferably about 2.0, while continuing to add whatever acid is required in order to maintain a pH of from about 4.0 to about 4.25. During cleaning and disinfection, samples are periodically collected and monitored for chlorine dioxide using standard analytical technique to determine chlorine dioxide {such as the diethyl-p-phenylene diamine test ("the DPD test") for free residual chlorine dioxide, expressed "as chlorine"} as well as determining the level of hardness present by complexometric titration.

During this two hour time period, chlorine dioxide concentrations are found to be in the range of from about 0.5 to about 1.0 ppm, expressed as free chlorine. Hardness values increase from 400 to 1600 ppm over a 2 hour period. After 2 hours, the acid feed is stopped and the system water pH is allowed to rise due to the increasing alkalinity within the system. A rapid rise in the pH is also achieved by the addition of enough caustic solution to bring the pH to about 5.0 to 6.5, preferably 5.5.

Sufficient sodium hexametaphosphate, used as a chelating agent, taken from the Ondeo Nalco chemical stockroom, is added to the system water such that its concentration in the water is from about 10 ppm to about 500 ppm, preferably 200 ppm.

Sufficient quantities of a non-oxidizing biocide 2,2-dibromo-3-nitrilopropionamide, taken from the Ondeo Nalco chemical stockroom, is added to the system water such that its concentration in the water is from about 1 ppm to about 20 ppm.

The system water pH is maintained at 5.5 with intermittent addition of glycolic acid, as needed. The system water blow-down was maintained per normal operational program and loss of chemical (sodium hexametaphosphate and 2,2-dibromo-3-nitrilopropionamide) following blow down was replenished by slug doses of the chemicals. The system water is recirculated for a period of about 48 hours. The total hardness levels are monitored periodically and when hardness level increases are minimal, the acid and biocide feed is stopped and the cleaning process is deemed completed. The system water is blown down to single cycles, and the routine water treatment program is reinstated. The industrial water system is returned to normal service.

A visual inspection of the water contact surfaces shows clean surfaces with no contamination. The method of on-line simultaneous cleaning and disinfection is deemed to be a success.

What is claimed is:

1. An on-line method of simultaneously cleaning and disinfecting an industrial water system comprising the steps of:
    a) providing an industrial water system; wherein said industrial water system is selected from the group consisting of cooling water systems and boiler water systems;
    b) adding a Compound selected from the group consisting of the alkali salts of chlorite and chlorate, or a mixture thereof, and optionally adding a corrosion inhibitor and optionally adding a dispersant to the water of said industrial water system; wherein enough Compound is added to reach a concentration of from about 1 ppm to about 1000 ppm, wherein if a corrosion inhibitor is added enough corrosion inhibitor is added to reach a concentration of from about 50 ppm to about 500 ppm and wherein if a dispersant is added enough dispersant is added to reach a concentration of from about 1 ppm to about 500 ppm;
    c) lowering the pH of the water in the industrial water system to about 4.0 by adding an acid selected from the group consisting of mineral acids and organic acids to the water of said industrial water system and maintaining the pH of the water in the industrial water system at about 4.0 for from about 1 to about 4 hours;
    d) adding a chelating agent to the water of the industrial water system, wherein enough chelating agent is added to maintain the concentration of the chelating agent at from about 10 ppm to about 500 ppm in the water of the industrial water system; wherein said chelating agent is added either before or after the optional next step of raising the pH;
    e) optionally raising the pH of the water in the industrial water system from about 5.5 to about 11;
    f) adding a biocide to the water of the industrial water system; wherein if the chelating agent is added after the optional step of raising the pH, then the chelating agent and the biocide from step g) may be added simultaneously to the water or the chelating agent may be added first followed by the biocide or the biocide may be added first, followed by the chelating agent; wherein the amount of biocide added is that amount sufficient to have a concentration of from about 1 ppm to about 500 ppm in the water of the industrial water system; and
    g) allowing the water in the industrial water system to circulate for an additional time period of from about 1 hour to about 120 hours.

2. The method of claim 1 further comprising: 1) modifying said industrial water system to a single cycle system after step a); 2) halting the feeding of chemical or biological treatment chemicals to the water of the industrial water system; and 3) adding said corrosion inhibitor and said dispersant to the industrial water system.

3. The method of claim 1 in which said corrosion inhibitor is benzotriazole.

4. The method of claim 1 in which said dispersant is a terpolymer comprising from about 30 to about 70 mol % acrylic acid, from about 10 to about 30 mol % acrylamide and from about 20 to about 40 mol % aminomethylsulfonic acid.

5. The method of claim 1 wherein the alkali salt of chlorite is sodium chlorite.

6. The method of claim 1 in which said acid is glycolic acid.

7. The method of claim 1 in which said chelating agent is sodium hexametaphosphate.

8. The method of claim 1 in which said biocide is 2,2-dibromo-3-nitrilopropionamide.

* * * * *